United States Patent [19]

Leach et al.

[11] 3,996,297
[45] Dec. 7, 1976

[54] PROCESS FOR PURIFICATION OF 2,6-XYLENOL

[75] Inventors: Bruce E. Leach; Charles M. Starks, both of Ponca City, Okla.

[73] Assignee: Continental Oil Company, Ponca City, Okla.

[22] Filed: Aug. 25, 1975

[21] Appl. No.: 607,734

[52] U.S. Cl. .................... 260/621 B; 260/627 G; 260/621 A; 260/624 A
[51] Int. Cl.² .................. C07C 39/06; C07C 37/38
[58] Field of Search ....... 260/621 R, 621 B, 621 A, 260/624 A, 627 G

[56] References Cited

UNITED STATES PATENTS

| | | | |
|---|---|---|---|
| 2,435,087 | 1/1948 | Luten | 260/627 G |
| 2,789,146 | 4/1957 | Neuworth | 260/627 G |
| 3,422,156 | 1/1969 | Thoma | 260/621 R |
| 3,426,358 | 2/1969 | Schlichting et al. | 260/621 R |

*Primary Examiner*—James O. Thomas, Jr.
*Assistant Examiner*—W. B. Lone
*Attorney, Agent, or Firm*—Cortlan R. Schupbach, Jr.

[57] ABSTRACT

A method is provided for separating 2,6-xylenol from m,p-cresols by treating the mixture with methanol over alumina catalysts at about 360° C and 400-500 psig.

4 Claims, No Drawings

PROCESS FOR PURIFICATION OF 2,6-XYLENOL

This invention relates to the methylation of the nucleus of hydroxy aromatic compounds with methanol in the liquid phase. More specifically, this invention relates to a process for purifying 2,6-xylenol from m,p-cresol mixtures by methylating m,p-cresols in liquid phase.

Pure 2,6-xylenol is a desirable chemical intermediate in many chemical reactions and as such has a higher value than impure 2,6-xylenol. Normally, the major impurity in 2,6-xylenol is m,p-cresol. Separation by fractional distillation is difficult because the boiling points for 2,6-xylenol, m-cresol, and p-cresol are 201.0°, 202.2°, and 201.1° C, respectively. The present practice is to use solvent extraction techniques which involve dissolving a feed material containing from 5 to 12 weight percent of m,p-cresol in toluene and contacting this feed material with approximately a 10 percent aqueous sodium hydroxide solution. The 2,6-xylenol and toluene phases are separated from the aqueous phase which contains the sodium salt of m,p-cresol. Acid is then added to the aqueous phase to recover m,p-cresol. The aqueous solution still contains some cresylic acid and must be treated prior to disposal. To complete the solvent extraction process, 2,6-xylenol is then distilled from toluene. Cresylic acid is a mixture of phenolic compounds.

Clearly this method is expensive. Major portions of acid and base are required, and problems of disposal of the cresylic acid are encountered. It would be very desirable to have a simpler, less expensive process for purifying 2,6-xylenol when contaminated with m,p-cresols.

It is therefore an object of the present invention to provide a method of purifying 2,6-xylenol from contamination with m,p-cresol. Other objects will become apparent to those skilled in this art as description proceeds.

In accordance with the objects of the present invention, there is provided a process for the purification of 2,6-xylenol from m,p-cresol impurities. Concisely stated, the process comprises contacting a mixture of 2,6-xylenol and m,p-cresols with from .1 to 1.0 mol ratio of a methylating agent by passing over an alumina catalyst at temperatures of about 320° to 390° C, under pressure conditions of 300 to 600 pounds per square inch gauge (psig) and liquid hourly space velocities (LHSV) of from 1 to 15. The process is effective when used alone but can, of course, be used in combination with solvent extraction processes.

While temperatures of from 320° to 390° C are practical, temperatures of from 335° to 365° C are preferred. Pressures of from 350 to 500 psig are also preferred. LHSV of from 3 to 10 are most preferred, while a methanol mol ratio of from 0.2 to 0.8 is most preferred.

The basis of the invention is converting m,p-cresol to 2,4/2,5- and 3,5-xylenols. 2,4/2,5- and 3,5-xylenols are easily separable from 2,6-xylenol by conventional fractional distillation methods. The 2,6-xylenol which has been purified can be recycled to still further increase the purity.

In carrying out the liquid phase methylation of the present invention, methanol is the preferred methylating agent. Other methylating agents can also be used. Examples of such methylating agents are alcohols such as ethanol and isopropanol and olefins such as propylene and isobutylene.

Catalysts preferred in the present invention are alumina catalysts generally. However, it has been discovered that catalysts derived from aluminum alkoxide hydrolysis appear to be more effective than those derived from other sources. Examples of such catalysts are CATAPAL catalysts and DISPAL catalysts produced by Continental Oil Company.

The present invention is more concretely described with reference to the examples below wherein all parts and percentages are by weight unless otherwise specified. The examples are intended to illustrate the present invention and are not to be construed to limit it.

In all examples below, the 2,6-xylenol and m,p-cresol mixture was mixed with methanol and passed over CATAPAL SB alumina extrudates in a ⅜-inch stainless steel reactor under pressure. Flow in the reactor was upward.

EXAMPLE 1

Typical distillation cuts which serve as feedstock for the production of 2,6-xylenol generally have the following composition.

TABLE I

| Component | Feed A Wt % | Feed B Wt % |
|---|---|---|
| o-Cresol | 1.0 | 0.5 |
| m,p-Cresol | 11.0 | 8.7 |
| 2,6-Xylenol | 88.0 | 90.0 |
| 2,4/2,5-Xylenol | — | 0.7 |
| 2,3/3,5-Xylenol | — | 0.1 |

Reaction of the two feedstocks shown in Table I with .5 mol ratio methanol, 400 psig back pressure, 355° C, and an LHSV of 6.0 gave products containing m,p-cresol and 2.6-xylenol percentages by weight as shown in Table II.

TABLE II

|  | A | B |
|---|---|---|
| m,p-Cresol | 0.8 | 0.9 |
| 2,6-Xylenol | 99.2 | 99.1 |

Material from A above (99.2 percent pure) was mixed four parts to one part with starting material as would occur in a plant operation containing recycle streams. m,p content of this feed material was 1.5 percent. Reaction with .5 mol ratio methanol resulted in a product having a purity of 99.6 percent.

Clearly, such a feed material would greatly reduce the costs of solvent extraction which include sodium hydroxide and acid requirements, or if another reaction cycle was run without adding high m,p-cresol content feed, very high purity of the extracted 2,6-xylenol should be achieved.

The effect of the catalyst on the process of the present invention can be exemplified by comparing the CATAPAL catalyst with catalysts such as HA1404 and HA1706, sold by Harshaw Chemical Company. Utilizing a feedstock containing 0.51 percent by weight o-cresol, 8.70 percent by weight m,p-cresols, and 89.99 percent by weight of 2,6-xylenol, it can be seen from Table III data that other alumina catalysts did not convert as much of the m,p-cresol as the CATAPAL type alumina.

TABLE III

|  | HA1404 | HA1706 | CATAPAL SB |
|---|---|---|---|
| m,p-Cresol | .83 | 2.11 | 0.35 |
| o-Cresol | 1.08 | .12 | 0.34 |
| 2,6-Xylenol | 77.35 | 79.07 | 69.83 |
| 2,4/2,5-Xylenol | 1.56 | 2.78 | 3.93 |

The remaining weight percentage products were directed towards 2,3,6-trimethyl phenol, 2,4,6-trimethyl phenol, 3,5-xylenol, and 2,3,4,6/2,3,5,6-tetramethyl phenol. It can be clearly seen from the data that the CATAPAL SB type alumina is more effective in the process of the present invention than alumina from other sources.

While certain embodiments and details have been shown for the purpose of illustrating this invention, it will be apparent to those skilled in this art that various changes and modifications may be made herein without departing from the spirit or the scope of the invention.

We claim:
1. A method for separating 2,6-xylenol from admixture with meta,para-cresols comprising methylating the meta,para-cresols with methanol over alumina catalysts to form 2,4/2,5-xylenol and 2,3/3,5-xylenol, and separating the 2,6-xylenol from the resulting mixture by distillation, wherein the methylation is carried out at a mole ratio of methanol to starting mixture of from about 0.2 to 1.0, a temperature of from about 320° C to 390° C, and a pressure of from about 300 to about 600 pounds per square inch gauge.
2. A method as described in claim 1 wherein the reaction is carried out in a continuous flow reactor.
3. A method as described in claim 2 wherein the liquid hourly space velocity is from about 1 to about 15.
4. A method as described in claim 1 wherein the alumina catalyst is derived from aluminum alkoxide hydrolysis.

* * * * *